United States Patent [19]
Mayer et al.

[11] Patent Number: 6,030,924
[45] Date of Patent: Feb. 29, 2000

[54] SOLID FORMULATIONS

[75] Inventors: Winfried Mayer, Bubenheim; Christian Wassmer, Niedersaulheim; Sandra Doerr, Bad Kreuznach, all of Germany

[73] Assignee: American Cyanamid Company, Madison, N.J.

[21] Appl. No.: 09/071,076

[22] Filed: May 1, 1998

Related U.S. Application Data

[60] Provisional application No. 60/049,412, Jun. 11, 1997.

[30] Foreign Application Priority Data

May 7, 1997 [EP] European Pat. Off. ............... 97107521

[51] Int. Cl.$^7$ ...................................................... A01N 25/12
[52] U.S. Cl. ........................... 504/116; 504/134; 504/257; 514/237.5; 514/436; 514/476; 514/494
[58] Field of Search ...................................... 504/116, 134, 504/257; 514/237.5, 436, 476, 494

[56] References Cited

U.S. PATENT DOCUMENTS 5,332,714  7/1994  Albrecht et al. ......................... 504/116
5,679,618  10/1997  Kocur ...................................... 504/116

FOREIGN PATENT DOCUMENTS

| 2091746 | 3/1992 | Canada . |
| 0184 582 | 11/1984 | European Pat. Off. . |
| 0447 004 A2 | 3/1991 | European Pat. Off. . |
| 1388924 | 3/1975 | United Kingdom . |
| WO 88/05630 | 8/1988 | WIPO . |
| WO 89/00079 | 1/1989 | WIPO . |
| WO 97/5777 | 2/1997 | WIPO . |

*Primary Examiner*—S. Mark Clardy
*Attorney, Agent, or Firm*—Barbara L. Renda

[57] ABSTRACT

The novel solid formulations obtained by low pressure extrusion of a mixture comprising

- at least one active ingredient; and
- at least one defoaming agent and/or foam breaking agent from the
- group consisting of perfluoroalkylphosphinic acids and/or perfluoroalkylphosphonic acids and/or their salts, show foam breaking activities even after extrusion, drying and storage at elevated temperatures and are thus very suitable for preparing tank mixtures for use in crop protection.

18 Claims, No Drawings

SOLID FORMULATIONS

This application is based upon European Application EP 97107521.3, filed May 7, 1997 and U.S. Provisional Application 60/049412, filed Jun. 11, 1997. Priority of each is hereby claimed under 35 U.S.C. § 119.

BACKGROUND OF THE INVENTION

Many solid crop protection agents are currently supplied in the form of wettable powders and granules. Typically, the herbicidal, fungicidal or insecticidal active ingredients are used together with inert fillers, such as chalk or kaolin, in particular surface active substances, in the preparation of such formulations so that the formulations are well wetted and dispersed in water. The inclusion of wetting agents lowers the surface tension of the spray mix. As a result, uniform wetting of the leaf surface is achieved. However, due to this lowered surface tension, these spray mixtures also tend to foam.

European patent application EP 0 561 265 suggests reduction of the tendency of foaming of such solid formulation by the addition of certain defoamer agents selected from the group of perfluoroalkylphosphinic acids and/or perfluoroalkylphosphonic acids and/or their salts. The formulations disclosed by this reference are prepared either by spray drying or fluidized bed granulation of aqueous suspensions containing the formulation ingredients. However, depending on the ingredients, the solid formulations obtained by spray drying or fluidized bed granulation exhibit higher tendency to develop dust when added to water in the spray tank. This results in end-users being exposed to higher dose rates of the active ingredient. The present invention provides solid formulations for crop protection with reduced tendency of foaming and dustiness.

SUMMARY OF THE INVENTION

The present invention provides a novel solid formulation obtained by low pressure extrusion of a mixture comprising
  at least one active ingredient; and
  at least one defoaming agent and/or foam breaking agent from the
  group consisting of perfluoroalkylphosphinic acids and/or
  perfluoroalkylphosphonic acids and/or their salts.

These formulations exhibit foam breaking activities even after extrusion, drying and storage of the formulation elevated temperatures and are thus advantageous for preparing tank mixtures for use in crop protection. Moreover, the new formulations possess a reduced tendency to develop dust when added to water in the spray tank.

The new formulations show an excellent activity and selectivity in various crops.

It is an object of the present invention to provide novel, solid formulations for crop protection which exhibit decreased foaming and decreased dusting during their use.

It is also an object of the invention to provide methods for controlling pests by contacting plants with a composition obtained by dispersing a solid formulation according to the invention.

These and other objects and features of the invention will be more apparent from the detailed description set forth hereinbelow, and from the appended claims.

DETAILED DESCRIPTION OF THE PREFERRED EMBODIMENTS

It has surprisingly been found that improved solid formulations for crop protection comprising
  at least one active ingredient; preferably two different active ingredients, and
  at least one defoaming agent and/or foam breaking agent from the
  group consisting of perfluoroalkylphosphinic acids and/or perfluoroalkylphosphonic acids and/or their salts, which are produced by low pressure extrusion, show reduced foaming and dustiness.

The active ingredient, which can be supplied in the form of the solid formulation according to the invention include all suitable biologically active compounds for plant protection, preferably fungicides, herbicides, insecticides, acaricides, nematicides and repellents. Active ingredients which are solid at room temperature are preferred.

Mixtures of different biologically active compounds can have a broader spectrum of activity than a single compound alone. Furthermore, these can exhibit a synergistic effect compared with the single active ingredients. In a preferred embodiment, the formulation of the present invention can be used with a mixture of active ingredients.

Preferred fungicides for use in the compositions of the present invention are the commercially available compounds selected from the group consisting of:
  anilazine, azoxystrobin, benalaxyl, benomyl, binapacryl, bitertanol, blasticidin S, Bordeaux mixture, bromuconazole, bupirimate, captafol, captan, carbendazim, carboxin, carpropamid, chlorbenzthiazon, chlorothalonil, chlozolinate, copper-containing compounds such as copper oxychloride, and copper sulfate, cycloheximide, cymoxanil, cypofuram, cyproconazole, cyprodinil, dichlofluanid, dichlone, dichloran, diclobutrazol, diclocymet, diclomezine, diethofencarb, difenoconazole, diflumetorim, dimethirimol, dimethomorph, diniconazole, dinocap, ditalimfos, dithianon, dodemorph, dodine, edifenphos, epoxiconazole, etaconazole, ethirimol, etridiazole, famoxadone, fenapanil, fenarimol, fenbuconazole, fenfuram, fenhexamid, fenpiclonil, fenpropidin, fenpropimorph, fentin, fentin acetate, fentin hydroxide, ferimzone, fluazinam, fludioxonil, flumetover, fluquinconazole, flusilazole, flusulfamide, flutolanil, flutriafol, folpet, fosetyl-aluminium, fuberidazole, furalaxyl, furametpyr, guazatine, hexaconazole, imazalil, iminoctadine, ipconazole, iprodione, isoprothiolane, kasugamycin, kitazin P, kresoxim-methyl, mancozeb, maneb, mepanipyrim, mepronil, metalaxyl, metconazole, methfuroxam, myclobutanil, neoasozin, nickel dimethyidithiocarbamate, nitrothalisopropyl, nuarimol, ofurace, organo mercury compounds, oxadixyl, oxycarboxin, penconazole, pencycuron, phenazineoxide, phthalide, polyoxin D, polyram, probenazole, prochloraz, procymidione, propamocarb, propiconazole, propineb, pyrazophos, pyrifenox, pyrimethanil, pyroquilon, pyroxyfur, quinomethionate, quinoxyfen, quintozene, spiroxamine, SSF-126, SSF-129, streptomycin, sulfur, tebuconazole, tecloftalame, tecnazene, tetraconazole, thiabendazole, thifluzamide, thiophanate-methyl, thiram, toiclofosmethyl, tolylfluanid, triadimefon, triadimenol, triazbutil, triazoxide, tricyclazole, tridemorph, triflumizole, triforine, triticonazole, validamycin A, vinclozolin, XRD-563, zarilamid, zineb, ziram.

In addition, the formulations according to the invention may contain at least one compound of the following classes of biological control agents such as viruses, bacteria, nematodes, fungi, and other microorganisms hich are suitable for the control of insects, weeds or plant diseases, or to induce host resistance in the plants. Examples of such biological control agents are: *Bacillus thuringiensis, Verticillium lecanii, Autographica californica* NPV, *Beauvaria bassiana, Ampelomyces quisqualis, Bacilis subtilis, Pseudomonas fluorescens, Steptomyces griseoviridis* and *Trichoderma harzianum*.

Moreover, the formulations according to the invention may contain at least one chemical agent that induces the systemic acquired resistance in plants such as, for example, nicotinic acid or derivatives thereof, 2,2-dichloro-3,3-dimethylcylopropylcarboxylic acid or BION.

Also preferred compositions can include derivatives of triazolopyrimidines which are disclosed, for example, by European patent application EP-A-0 550 113.

Another group of preferred fungicidal compounds are the benzoylbenzenes which are disclosed, for example, by European patent application EP-A-0 727 141.

Preferred herbicides are the commercially available compounds selected from the group consisting of:

2,4-D, 2,4-DB, 2,4-DP, acetochlor, acifluorfen, alachlor, alloxydim, ametrydione, amidosulfuron, asulam, atrazin, azimsulfuron, benfuresate, bensulfuron, bentazon, bifenox, bromobutide, bromoxynil, butachlor, cafenstrole, carfentrazone, chloridazon, chlorimuron, chlorpropham, chlorsulfuron, chlortoluron, cinmethylin, cinosulfuron, clomazone, clopyralid, cyanazin, cycloate, cyclosulfamuron, cycloxydim, daimuron, desmedipham, di-methazone, dicamba, dichlobenil, diclofop, diflufenican, dimethenamid, dithiopyr, diuron, eptame, esprocarb, ethiozin, fenoxaprop, flamprop-M-isopropyl, flamprop-M-methyl fluazifop, fluometuron, fluoroglycofen, fluridone, fluroxypyr, flurtamone, fluthiamid, fomesafen, glufosinate, glyphosate, halosafen, haloxyfop, hexazinone, imazamethabenz, imazamethapyr, imazamox, imazapyr, imazaquin, imazethapyr, ioxynil, isoproturon, isoxaben, isoxaflutole, lactofen, MCPA, MCPP, mefenacet, metabenzthiazuron, metamitron, metazachlor, methyidimron, metolachlor, metribuzin, metsulfuron, molinate, nicosulfuron, norflurazon, oryzalin, oxadiargyl, oxasulfuron, oxyfluorfen, pendimethalin, picloram, pretilachlor, propachlor, propanil, prosulfocarb, pyrazosulfuron, pyridate, qinmerac, quinchlorac, quizalofopethyl, sethoxydim, simetryne, sulcotrione, sulfentrazone, sulfosate, terbutryne, terbutylazin, thiameturon, thifensulfuron, thiobencarb, tralkoxydim, triallate, triasulfuron, tribenuron, triclopyr, trifluralin.

Furthermore preferred are the derivatives of aryloxypicolineamides which are disclosed, for example, by European patent application EP-A-0 447 004, in particular, N-(4-fluorophenyl) 6-(3-trifluoromethylphenoxy)-pyrid-2-ylcarboxamide having the proposed common name picolinafen.

Preferred insecticides are the commercially available compounds selected from the group consisting of:

pyrethroids such as deltamethrin, acrinathrin, tralomethrin, permethrin and cypermethrin, benzoylureas such as diflubenzuron and teflubenzuron, and active substances such as endosulfan and pirimicarb.

The active ingredients used in the formulation according to the present invention may be solid or fluid, preferably they are solid. In the case of fluid active ingredients the formulation according to the invention contains as a rule a solid auxiliary with absorbing properties.

The content of the active ingredient is, as a rule, 30 to 90% by weight, preferably 50 to 87% by weight, and, in particular, 70 to 85% by weight of total composition. Suitable defoaming and/or foam breaking agents are perfluoro($C_6$–$C_{12}$)alkylphosphinic acids and/or perfluoro($C_6$–$C_2$) alkylphosphonic acids and/or their alkali metal salts, such as sodium or potasssium salts, their ammonium salts, and their ($C_2$–$C_{16}$)alkylammonium salts. These defoaming and/or foam breaking agents are commercially available, for example, Fluowet PP, a mixture of perfluoro($C_6$–$C_{12}$) alkylphosphinic acids and perfluoro($C_6$–$C_{12}$) alkylphosphonic acids, (commercially available from Clariant GmbH, formerly Hoechst AG, Germany) or can be prepared by known methods (DE 21 11 167). Particularly preferred are aqueous solutions of mixtures of perfluoro ($C_6$–$C_{12}$)alkylphosphinic acids and perfluoro($C_6$–$C_{12}$) alkylphosphonic acids, which are commercially available as, for example, Defoamer SF (commercially available from Clariant GmbH, formerly Hoechst AG, Germany). These aqueous solutions can easily be incorporated into the formulation in the wetting step of the process.

The proportion of the antifoam or foam breaking agent in the formulation can be up to 10% by weight. As a rule, 0.05 to 10% by weight, preferably 0.07 to 4% by weight, and, in particular, 0.08 to 0.50% by weight are used.

Specific embodiments of the invention include:

(a) A solid formulation obtained by a process which comprises the steps of: wetting the powder base of the active ingredient with a mixture of the defoaming agent and/or foam breaking agent and water, in particular, with an aqueous solution of the defoaming and/or foam breaking agent;

extrusion of the wetted powder on an extruder, in particular, on a radial twin screw extruder, a basket extruder or a mono or twin dome extruder; and drying the resulting granules in a fluidized bed dryer.

(b) A solid formulation, wherein the powder base of the active ingredient comprises, in addition to the said constituents, further formulation auxiliaries selected from the group consisting of dispersants, agglomeration auxiliaries, stabilizers, wetting agents, disintegrants and fillers.

(c) A solid formulation essentially consisting of 25 to 90% by weight of at least one active ingredient, 0.05 to 10% by weight of said defoaming agent and/or foam breaking agent, 0 to 45% by weight of a filler;

5 to 50% by weight of one or more dispersants, agglomeration auxiliaries, one or more wetting agent, one or more disintegrants and/or one or more stabilizers.

In a particular preferred embodiment the formulation according to this invention contain 0–5% by weight of a filler and 10–25% by weight of solid dispersant.

(d) A solid formulation wherein said active ingredient comprises an E/Z mixture of an acrylic acid morpholide fungicide of the following structure:

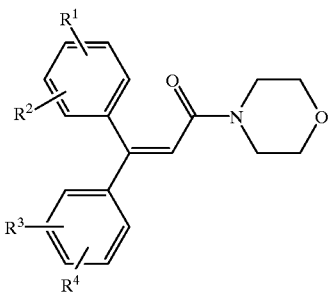

in which

R$^1$ and R$^2$ each independently represent a hydrogen atom or an alkyl, alkenyl, alkynyl, alkadienyl, haloalkyl or alkoxy group, preferably a C$_{1-6}$ alkoxy group, in particular a methoxy group, and R$^3$ and R$^4$ each independently represent a hydrogen or a halogen atom or an alkyl or alkoxy group, preferably a hydrogen or chloro atom, in particular wherein said active ingredient is a dimethomorph (coded DMM) or a mixture of DMM and mancozeb (coded MZ) and/or dithianon (coded DI).

(e) A solid formulation wherein said active ingredient comprises an aryloxypicolinamide herbicide of the following structure:

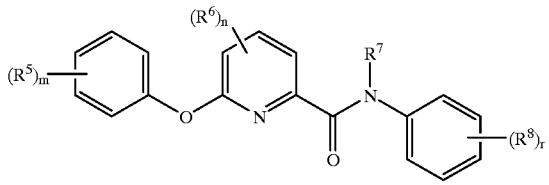

in which

R$^5$ and R$^8$ each independently represent a halogen atom or an alkyl, or haloalkyl group, preferably a fluoro or chloro atom or a C$_{1-6}$ fluoroalkyl group, in particular a fluoro atom or a trifluoromethyl group, and R$^6$ represents a halogen atom or an alkyl or alkoxy group, preferably a C$_{1-6}$ alkyl or a C$_{1-6}$ alkoxy group, in particular a methyl or methoxy group, R$^7$ represents a hydrogen atom or an alkyl group, in particular a hydrogen atom or a methyl group, m and r each independently represent 1, 2 or 3, preferably 1 or 2, in particular 1, and n represents 0 or 1, in particular 0.

Particularly preferred are the solid formulations wherein the active ingredient is picolinafen (coded PN), or a mixture of PN and cyanazine (coded CY) and/or pendimethalin (coded PD).

(f) The solid formulation which is water-dispersible granules.

Depending on the active ingredient used, the powder base comprising the active ingredient is wetted with an aqueous solution of the defoamer and 10 to 35% by weight, preferably 12 to 30% by weight, in particular 14 to 29.5% by weight of water by spraying the solution on the agitated powder.

The wetted material is a non-dusty and flowable mass and is used as the feedstock for the granulation process in the low-pressure extruder.

Suitable extruders include axial and radial designs with single or twin screws, and roll-type extrusion presses. A twin screw extrusion has proven to be most useful. During the extrusion process, the extruder is preferably cooled to temperatures below 40° C., in particular, by a flow of cooling water at the extruder head with water temperatures being between and 25° C.

The premix is extruded through a die or screen. The die holes range in diameter from 0.25 to 7 mm, and preferably, from 0.4 mm to 2 mm.

As a rule, the extrusion takes place at a pressure of up to 50 bar, preferably, up to 30 bar, and in particular, up to 20 bar.

The cylindrical granules formed during the extrusion process are dried to a water content less than 3% by weight, preferably less than 2.5%, and in particular about 2% by weight.

The drying process is preferably carried out with a fluidised bed dryer at temperatures between 60° C. and 80° C., preferably, between 65° C. and 75° C., and, in particular at about 70° C.

After drying, the product is preferably sieved on 0.4 and 2.0 mm sieves.

Suitable dispersants may be so-called water-soluble soaps, as well as water-soluble synthetic surface-active compounds. Soaps usually are alkali, earth alkali or optionally substituted ammonium salts of higher fatty acids (C$_{10}$–C$_{20}$), e.g., the sodium or potassium salts of oleic or stearic acid or of mixtures of natural fatty acids which are prepared, for example, from coconut or tallow oil. Furthermore, methyl-taurine salts of fatty acids may be used. However, so-called synthetic surfactants are preferably used, especially fatty sulfonates, fatty sulfates or alkyl aryl sulfonates. The fatty sulfates or fatty sulfonates are normally used as alkali, earth alkali or optionally substituted ammonium salts and have an alkyl moiety of 8 to 22 carbon atoms, whereby alkyl also means the alkyl moiety of acyl residues, such as the sodium or calcium salt of lignin sulfonic acid, of sulfuric acid dodecylate, or of a mixture of fatty alcohols prepared from natural fatty acids, in particular, sodium lignin sulfonate. This also includes the salts of sulfuric acid esters, sulfonic acids and adducts of fatty alcohols and ethylene oxide. Alkyl aryl sulfonates are, for example, the sodium, calcium or triethyl ammonium salts of dodecyl benzene sulfonic acid, dibutyl naphthalene sulfonic acid or of a condensate of naphthalene sulfonic acid and formaldehyde. Furthermore, phosphates, such as the salts of the phosphoric acid ester of a p-nonylphenol-(4–14)-ethylene oxide adduct or phospholipids, may be used. In addition, non-ionic dispersants may be used. Preferred are block polymers obtainable from propylene oxide and ethylene oxide, in particular, block polymers which consist of a polyoxypropylene core having a molecular weight of about 3,000 to about 3,500 and the remainder having a combined molecular weight of about 6,000 to 7,000 comprising ethylene oxide units.

In preferred embodiments, the dispersants are selected from the commercially available components:

Tensiofix LX special, a sodium lignin sufonate available from Omnichem S.A., 1348 Louvain-La-Neuve, Belgium;

Ufoxane 3 A, a sodium lignin sufonate available from Borregaard;

Borresperse NH, an ammonium lignin sufonate (available from Borregaard);

Geropon TA/72, a sodium polycarboxylate, (available from Rhodia, formerly Rhone-Poulenc);

Soprophor AS/222, an ethoxylated fatty alcohol adsorbed on silica, (available from Rhodia formerly Rhone-Poulenc); and Pluronic PE 10500, a block polymer obtained from propylene oxide and ethylene oxide, (available from BASF Corporation).

The solid formulation according to the present invention preferably comprises 5 to 25% by weight, in particular 7.5 to 15% of at least one dispersant.

Suitable wetting agents are, as a rule, salts of long chained alkyl sulfates. The fatty sulfates are normally used as alkali, earth alkali or optionally substituted ammonium salts and have an alkyl moiety of 8 to 22 carbon atoms. Particularly preferred is sodium lauryl sulfate, commercially obtainable as Tensiofix BCZ, a sodium alkyl sulfate, available from Omnichem S.A., 1348 Louvain-La-Neuve, Belgium or as Rewopol NLS 90 available from Witco GmbH, Germany.

The solid formulation according to the present invention preferably comprises 1 to 10% by weight, in particular, 2 to 5% of at least one wetting agent.

The surfactants and wetting agents generally used for compositions of the invention are disclosed in publications such as:

"McCutheon's Detergents and Emulsifiers Annual", MC Publishing Corp., Ridgewood, N.J., USA 1981;

H. Stache, "Tensid-Taschenbuch", 2nd ed., C. Hanser, Munich, Vienna, 1981;

M. and J. Ash, "Encyclopedia of Surfactants", Vol. I–III, Chemical Publishing Co., New York, N.Y., USA 1980–1981.

Conventionally used fillers may be used in the solid formulation according to the present invention. Preferably used are such solid matters, which are essentially insoluble in water and have large surfaces and/or high absorbencies, in particular, natural mineral powders such as kaolin, argillaceous earth, talcum, chalk, quartz, atapulgite, montmorillonite and synthetic mineral powders such as silicic acid, alumina, silicates, in particular kaolin, or Clay GTY, a mixture of inorganic minerals, which is commercially available from EEC Int. Ltd., UK.

The solid formulation according to the present invention preferably comprises 0 to 45% by weight of at least one filler, in particular, 20 to 40% of Clay GTY and a content of less than 7.0% by weight of a solid dispersant.

A major advantage of the solid formulations of the present invention results from the low amounts of kaolin required, if the formulation comprises high amounts of active ingredients, preferably more than 60% by weight, in particular 70 to 90% by weight and/or high amounts of a solid dispersant, preferably 7.0–25.0% by weight, in particular 8.0–15.0% by weight. The inventive solid formulations contain, as a rule, less than 10% by weight, and preferably less than 6% by weight of kaolin. In a highly preferred embodiment, no kaolin is necessary at all.

Conventionally used disintegrants may be used in the solid formulation according to the present invention. Preferably, such solid matters, which are highly soluble in water, in particular, salts such as potassium sulfate, ammonium sulfate, potassium carbonate, sodium hydrogencarbonate and sodium acetate trihydrate are utilized.

The solid formulation according to the present invention preferably comprises 1 to 10% by weight, in particular, 1 to 7.5% by weight of at least one disintegrant. In a preferred embodiment, the solid formulation of the present invention contains 2 to 5% by weight of an alkali metal or ammonium sulfate or an alkali metal acetate trihydrate as disintegrant.

In a preferred embodiment of the present invention, the water dispersible granules obtained by low pressure extrusion essentially consist of 75 to 85% by weight of one or a mixture of two fungicides, 0.05 to 0.30% by weight of a mixture of perfluoro $(C_6-C_{12})$alkylphosphinic acids and perfluoro$(C_6-C_{12})$ alkylphosphonic acids, 7.5 to 15% by weight of a lignin sulfonate as dispersant, 1 to 5% by weight of an alkali metal or ammonium sulfate as disintegrant, and 1 to 5% by weight of lauryl sulfate as wetting agent.

In another preferred embodiment of the present invention the water dispersible granules obtainable by low pressure extrusion essentially consist of 70 to 85% by weight of one or a mixture of two herbicides, 0.05 to 0.35% by weight of a mixture of perfluoro $(C_6-C_{12})$ alkylphosphinic acids and perfluoro$(C_6-C_{12})$ alkylphosphonic acids, 5 to 10% by weight of a lignin sulfonate as dispersant, 0.5 to 5% by weight of a polycarboxylate as dispersant, 0.5 to 5% by weight of a propylene/ethylene oxide block polymer as dispersant, 1 to 7.5% by weight of an alkali metal acetate as disintegrant, 0.1 to 7.5% by weight of kaolin as filler, and 1 to 5% by weight of lauryl sulfate as wetting agent.

Furthermore, the invention relates to a method of combating pests at a locus which comprises treating the locus with a composition obtained by dispersing a solid formulation according to the invention in water.

Moreover, the invention relates to the use of a solid formulation according to the invention for the preparation of liquid aqueous formulations or spray mixtures.

As commodities, the inventive solid formulations may preferably be in a pure, undiluted form whereas the end-user generally employs diluted compositions. Said compositions may be diluted to a concentration of 0.001% of active ingredient (a.i.). The doses usually are in the range of about 0.01 to 10 kg a.i./ha, preferably in the range of 0.1 to 4.0 kg a.i./ha.

Said compositions may also comprise other auxiliaries such as stabilizers, viscosity controlling agents, thickeners, adhesives, fertilizers or other active ingredients to obtain special effects.

For a clearer understanding of the invention, the following specific examples are set forth below. These examples are merely illustrations and are not to be understood as limiting the scope and underlying principles of the invention in any way. Indeed, various modifications of the invention in addition to those shown and described herein will become apparent to those skilled in the art from the following examples and foregoing description. Such modifications are also intended to fall within the scope of the appended claims.

EXAMPLE 1

Dimethomorph/Mancozeb 90/600 WG

Prior to the extrusion process different powder bases have been prepared consisting of:

| ingredient | Powder Base A quantity (g) | Powder Base B quantity (g) |
|---|---|---|
| dimethomorph | 450 | 450 |
| Tensiofix BCZ | 150 | 150 |
| Tensiofix LX special | to 1000 | to 1000 |
| ammonium sulfate | — | 100 |

These Powder bases have been admixed with mancozeb as a second active ingredient as follows:

| ingredient | quantity (g) |
|---|---|
| Powder Mixture A | |
| powder base A | 200 |
| mancozeb 85% w/w | 706 |
| Tensiofix LX special | to 1000 |
| Powder Mixture B | |
| powder base B | 200 |
| mancozeb 85% w/w | 706 |
| ammonium sulfage | 20 |
| Tensiofix LX special | to 1000 |

The resulting powder mixtures are wetted with water (20 to 30% w/w) containing 1.8 g of a mixture of perfluoro($C_6$, $C_8$, $C_{10}$)alkylphosphinic acids and perfluoro($C_6$, $C_8$, $C_{10}$) alkylphosphonic acids, which has been obtained by diluting Defoamer SF (obtainable from Clariant GmbH, formerly Hoechst AG, Germany) with water.

The wetting process is carried out in a Drais annular mixer or, alternatively, a Lödige mixer. The wetted material is a non-dusty flowable mass which is used without delay as the feedstock for the extrusion process.

The granulation is carried out by means of extrusion technique using a Twin screw extruder with a throughput rate of 70 to 100 kg/h at a pressure of 0–30 bar. The extruder head is cooled with water to 20° C. The grid diameter is 1 mm. The resulting extruded mass is dried with a fluidized bed dryer at a temperature of about 70° C. to achieve a water content of less than 2.5% by weight. After drying, the product is sieved on 0.4 and 2.0 sieves. The obtained yellowish solid product has a bulk density of 678 kg/m³. The cylindrical granules formed show a porous surface.

Further physical properties of the resulting product are given in the following Tables I to VI. The formulation has been stored at different temperatures (20, 30 or 40° C.) in block bottom bags or at elevated temperature of about 54° C. under pressure.

TABLE I

| | Active Suspensibility | | | |
|---|---|---|---|---|
| | Active suspensibility at a dilution of | | | |
| | 0.5% w/v | | 0.2% w/v | |
| | DMM | MZ | DMM | MZ |
| Initial | 93 | 99 | 92 | 96 |
| 2 weeks at 54° C. | 93 | 98 | 91 | 91 |
| 8 weeks at 40° C. | 93 | 95 | 93 | 95 |
| 26 weeks at 20° C. | 88 | 93 | 88 | 92 |
| 26 weeks at 30° C. | 87 | 90 | 87 | 90 |

TABLE II

| | Dispersibility |
|---|---|
| | Dispersibility [%] |
| Initial | 90 |
| 2 weeks at 54° C. | 87 |
| 8 weeks at 40° C. | 86 |
| 26 weeks at 20° C. | 92 |
| 26 weeks at 30° C. | 89 |

TABLE III

| | Wet sieving |
|---|---|
| | Residue on 75 μm [% w/w] |
| Initial | 0.06 |
| 2 weeks at 54° C. | 0.07 |
| 8 weeks at 40° C. | 0.05 |
| 26 weeks at 20° C. | 0.05 |
| 26 weeks at 30° C. | 0.03 |

TABLE IV

| | Persistent foaming | |
|---|---|---|
| | foam [ml] | |
| | directly | after 1 min. |
| Initial | 15 | <1 |
| 8 weeks at 40° C. | 28 | 0 |
| 26 weeks at 20° C. | 30 | 0 |
| 26 weeks at 30° C. | 30 | 0 |

TABLE V

| | Dustiness |
|---|---|
| | [mg] dust/30 g of granules |
| Initial | 5 |
| 8 weeks at 40° C. | 2 |
| 26 weeks at 20° C. | 1 |
| 26 weeks at 30° C. | 1 |

TABLE VI

| Dry sieve analysis | |
|---|---|
| Particle size [μm] | Distribution [% w/w] |
| >2000 | 0.0 |
| 1000–2000 | 78.6 |
| 500–1000 | 20.3 |

TABLE VI-continued

| Dry sieve analysis | |
|---|---|
| Particle size [μm] | Distribution [% w/w] |
| 250–500 | 0.2 |
| 125–250 | <0.1 |
| <125 | <0.1 |

It can be seen from Table IV that the foam breaking activity of the defoaming agent is given directly after the preparation of the solid formulation, even after longer term storage at 20° C., 30° C. or 40° C.

Lower concentrations of the defoamer in the composition result in similar activity. Solid water dispersible granules obtained by the same methods described above, but containing 0.08%, 0.10% or 0.30% by weight of the same defoamer show similar foam breaking activities.

As seen from Table V, the water dispersible granules according to the present invention exhibit very low dustiness.

Comparison-Example 1
Dimethomorph/Mancozeb 90/600 WG

Water dispersible granules are prepared according to the method described in Example 1, in which the defoamer has been replaced by different silicon based antifoam powders (Wacker ASP 13, 20, 30, commercially available from Wacker, Germany). These are far less active upon extrusion as can be seen from Table VII, which shows the initial foam formation achieved with these products 1 minute after mixing:

TABLE VII

| Persistent foaming | |
|---|---|
| Defoamer | foam [ml] |
| ASP 13 | >80 |
| ASP 20 | 20 |
| ASP 30 | 10 |

In addition, Wacker ASP 30 is loses its foam breaking activity upon storage of the solid formulation for 14 days at 54° C. completely (persistent foam formation of >80 ml after 1 minute).

Comparison-Example 2
Dimethomorph/Mancozeb 90/600 WG

Water dispersible granules are prepared according to the method described in Example 1, in which the defoamer has been replaced by Foammaster PD-1 (commercially available from Henkel KGaA, Germany), a blend of polyalkylene glycol and mineral hydrocarbons absorbed on an amorphous silica carrier. This is not active upon extrusion(persistent foam formation of >80 ml after 1 minute).

EXAMPLE 2
Dimethomorph/Dithianon 150/350 WG

Prior to the extrusion process different powder bases are prepared consisting of:

| ingredient | Powder Base C quantity (g) | Powder Base D quantity (g) |
|---|---|---|
| dimethomorph (DMM) | 600 | 0 |
| dithianon | 0 | 700 |
| Rewopol NLS 90 | 200 | 0 |
| Clay GTY | 200 | 100 |
| Borresperse NH | 0 | 150 |
| ammonium sulfate | 0 | 50 |

These Powder bases are mixed together as follows:

| Powder Mixture A | |
|---|---|
| ingredient | quantity (g) |
| powder base C | 250 |
| powder base D | 500 |
| Borresperse NH | 5 |
| Clay GTY | 245 |

The resulting powder mixtures are wetted with water (15 to 20% 10 w/w) containing 1.0 g of a mixture of perfluoro ($C_6$, $C_8$, $C_{10}$)alkylphosphinic acids and perfluoro($C_6$, $C_8$, $C_{10}$)alkylphosphonic acids, which has been obtained by diluting Defoamer SF (obtainable from Clariant GmbH, formerly Hoechst AG, Germany) with water.

The wetting process is carried out in a Drais annular mixer or, alternatively, a Löbdige mixer. The wetted material is a non-dusty flowable mass which is used without delay as the feedstock for the extrusion process.

The granulation is carried out by means of extrusion technique using a Twin screw extruder with a throughput rate of 70 to 100 kg/h at a pressure of 0–30 bar. The extruder head is cooled with water to 20° C. The grid diameter is 1 mm. The resulting extruded mass is dried with a fluidized bed dryer at a temperature of about 70° C. to achieve a water content of less than 1% by weight. After drying the product is sieved on 0.4 and 2.0 sieves. The obtained yellowish solid product has a bulk density of 570 kg/m$^3$. The cylindrical granules formed show a porous surface.

Further physical properties of the resulting product are given in the following Tables VIII to XII:

TABLE VIII

| Active Suspensibility | | |
|---|---|---|
| | DMM | dithianon |
| Initial | 97 | 82 |
| 2 weeks at 54° C. | 97 | 84 |

TABLE IX

| Dispersibility | |
|---|---|
| | Dispersibility [%] |
| Initial | 96 |
| 2 weeks at 54° C. | 98 |

TABLE X

Wet sieving

|  | Residue on 75 μm [% w/w] |
| --- | --- |
| Initial | 0.04 |
| 2 weeks at 54° C. | 0.04 |

TABLE XI

Persistent foaming

|  | foam [ml] |
| --- | --- |
| Initial | 0 |
| 2 weeks at 54° C. | 0 |

TABLE XII

Dustiness

|  | [mg] dust/30 g of granules |
| --- | --- |
| Initial | 9 |
| 2 weeks at 54° C. | 5 |

EXAMPLE 3

Picolinafen 750 WG (PI)

Prior to the extrusion process a powder base is prepared consisting f:

| ingredient | quantity (g) |
| --- | --- |
| Picolinafen (PI) | 750 |
| Ufoxane 3 A | 80 |
| Geropon TA/72 | 20 |
| Soprophor AS/222 | 20 |
| Pluronic PE 10500 | 20 |
| sodium acetate trihydrate | 50 |
| kaolin | 57 |

The resulting powder mixtures are wetted with water (20 to 30% w/w) containing 3.0 g of a mixture of perfluoro($C_6$, $C_8$, $C_{10}$)alkylphosphinic acids and perfluoro($C_6$, $C_8$, $C_{10}$) alkylphosphonic acids, which has been obtained by diluting Defoamer SF obtainable from Clariant GmbH former Hoechst AG, Germany with water.

The wetting process is carried out in a Drais annular mixer or, alternatively, a Lödige mixer. The wetted material is a non-dusty flowable mass which is used without delay as the feedstock for the extrusion process.

The granulation is carried out by means of extrusion technique using a Twin screw extruder with a throughput rate of 70 to 100 kg/h. The extruder head is cooled with water to 20° C. The grid diameter is 1 mm. The resulting extruded mass is dried with a fluidized bed dryer at a temperature of about 70° C. to achieve a water content of less than 2.5% by weight. After drying the product is sieved on 0.4 and 2.0 sieves.

The foaming behaviour of the formulation according to the invention has been tested by adding 0.11 g of said formulation to 250 ml water and measuring the volume of the foam formed in comparison to a formulation which has been prepared without Defoamer SF. The results are shown in Table XIII:

TABLE XIII

Foaming Behaviour

|  | Formulation without Defoamer SF | Formulation containing Defoamer SF |
| --- | --- | --- |
| Foam after 10 s | 10 ml | 8 ml |
| Foam after 1 minute | 10 ml | 5 ml |
| Foam after 3 minutes | 10 ml | 3 ml |
| Foam after 12 minutes | 10 ml | 3 ml |

EXAMPLE 4

Picolinafen/Cyanazine 150/600 WG

Prior to the extrusion process a powder base has been prepared consisting of:

| ingredient | quantity (g) |
| --- | --- |
| Picolinafen (PI) | 150 |
| Cyanazine (CY) | 600 |
| Ufoxane 3 A | 80 |
| Geropon TA/72 | 20 |
| Soprophor AS/222 | 20 |
| Pluronic PE 10500 | 20 |
| sodium acetate trihydrate | 50 |
| kaolin | 57 |

The resulting powder mixtures are wetted with water (20 to 30% w/w) containing 3.0 g of a mixture of perfluoro($C_6$, $C_8$, $C_{10}$)alkylphosphinic acids and perfluoro($C_6$, $C_8$, $C_{10}$) alkylphosphonic acids, which has been obtained by diluting Defoamer SF (obtainable from Hoechst AG, Germany) with water.

The wetting process is carried out in a Drais annular mixer or, alternatively, a Lödige mixer. The wetted material is a non-dusty flowable mass which is used without delay as the feedstock for the extrusion process.

The granulation is carried out by means of extrusion technique using a Twin screw extruder with a throughput rate of 70 to 100 kg/h. The extruder head is cooled with water to 20° C. The grid diameter is 1 mm. The resulting extruded mass is dried with a fluidized bed dryer at a temperature of about 70° C. to achieve a water content of less than 2.5% by weight. After drying the product is sieved on 0.4 and 2.0 sieves.

What is claimed is:

1. A low dustiness water-dispersible granule formulation for use in crop protection comprising at least one active ingredient; and at least one defoaming agent and/or foam breaking agent selected from the group consisting of perfluoroalkylphosphinic acids and/or perfluoroalkylphosphonic acids and/or their salts prepared by a process which comprises the steps of:

wetting a powder base containing said active ingredient with a mixture of said defoaming agents and/or foam breaking agents and water;

extrusion of the wetted powder on an extruder at a pressure of up to 50 bar through a die or screen; and drying the resulting granules in a fluidized bed dryer.

2. A process for the manufacture of a low dustiness water-dispersible granule formulation which comprises the steps of:

wetting a powder base containing of one or more active ingredients with a mixture of one or more defoaming agents and/or foam breaking agents selected from the group consisting of perfluoroalkylphosphinic acids and/or perfluoroalkylphosphonic acids and/or their salts and water;

extrusion of the wetted powder on an extruder at a pressure of up to 50 bar through a die or screen; and drying the resulting granules.

3. A formulation according to claim 1 obtainable by extrusion on a radial twin screw extruder, a basket extruder or a mono or twin dome extruder.

4. A formulation according to claim 1 obtainable by extrusion on a radial twin screw extruder, a basket extruder or a mono or twin dome extruder.

5. A formulation according to claim 1 wherein powder base of the active ingredient comprises, in addition to the said constituents, further formulation auxiliaries selected from the group consisting of dispersants, agglomeration auxiliaries, disintegrants, stabilizers, wetting agents and fillers.

6. A formulation according to claim 5 comprising 0 to 5% by weight of kaolin as filler, and 10 to 25% by weight of a solid dispersant.

7. A formulation according to claim 1 comprising 0.05 to 10% by weight of said defoaming agent and/or foam breaking agent.

8. A formulation according to claim 1 comprising a lignin sulfonate as dispersant.

9. A formulation according to claim 1 consisting of 25 to 90% by weight of at least one active ingredient, 0.05 to 10% by weight of of said defoaming agent and/or foam breaking agent, 0 to 45% by weight of a filler;

5 to 50% by weight of one or more dispersants, one or more disintegrants, one or more wetting agents and/or one or more s stabilizers.

10. A formulation according to claim 1 wherein said active ingredient is a fungicide or a mixture of at least two fungicides.

11. A formulation according to claim 1 wherein said active ingredient is an E/Z mixture of an acrylic acid morpholide fungicide of the following structure:

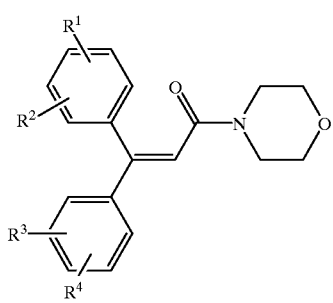

in which $R^1$ and $R^2$ each independently represent hydrogen atom or an alkyl, alkenyl, alkynyl, alkadienyl, haloalkyl, alkoxy, and $R^3$ and $R^4$ each independently represent a hydrogen or a halogen atom or an alkyl or alkoxy group.

12. A formulation according to claim 11 wherein said fungicide is a mixture of dimethomorph with mancozeb or dithianon.

13. A formulation according to claim 1 wherein said active ingredient is an aryloxypicolinamide herbicide of the following structure:

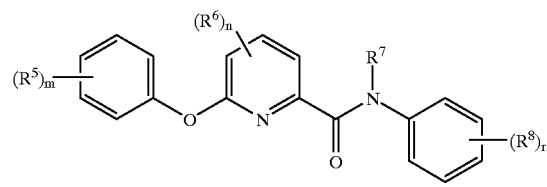

in which $R^5$ and $R^8$ each independently represent a halogen atom or an alkyl, or haloalkyl group, and $R^6$ represents a halogen atom or an alkyl or alkoxy group, $R^7$ represents a hydrogen atom or an alkyl group, m and r each independently represent 1, 2 or 3, and n represents 0 or 1.

14. A formulation according to claim 13 wherein said herbicide is picolinafen or a mixture of picolinafen and cyanazine.

15. A method of combating pests at a locus which comprises treating the locus with a composition obtained by dispersing a formulation of claim 1.

16. A method of combating pests at a locus which comprises treating the locus with a composition obtained by dispersing a formulation of claim 10.

17. A method of combating pests at a locus which comprises treating the locus with a composition obtained by dispersing a formulation of claim 12.

18. A method of combating pests at a locus which comprises treating the locus with a composition obtained by dispersing a formulation of claim 14.

* * * * *